United States Patent
Lyster et al.

(10) Patent No.: US 7,062,321 B2
(45) Date of Patent: Jun. 13, 2006

(54) METHOD AND APPARATUS FOR DEFIBRILLATING PATIENTS OF ALL AGES

(75) Inventors: Thomas D. Lyster, Bothell, WA (US); Thomas Solosko, Issaquah, WA (US); Carlton B. Morgan, Bainbridge Island, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 381 days.

(21) Appl. No.: 09/954,574

(22) Filed: Sep. 14, 2001

(65) Prior Publication Data

US 2003/0055459 A1 Mar. 20, 2003

(51) Int. Cl.
*A61N 1/39* (2006.01)
(52) U.S. Cl. .......................... 607/5; 607/142
(58) Field of Classification Search ............... 607/5, 607/7, 8, 4
See application file for complete search history.

(56) References Cited

U.S. PATENT DOCUMENTS

| | | | | |
|---|---|---|---|---|
| 4,895,169 A | * | 1/1990 | Heath | 607/142 |
| 5,697,955 A | * | 12/1997 | Stolte | 607/5 |
| 5,824,033 A | * | 10/1998 | Ferrari | 607/142 |
| 6,047,212 A | | 4/2000 | Gliner et al. | |
| 6,101,413 A | * | 8/2000 | Olson et al. | 607/5 |
| 6,125,298 A | * | 9/2000 | Olson et al. | 607/5 |
| 6,134,468 A | * | 10/2000 | Morgan et al. | 607/5 |
| 6,240,323 B1 | | 5/2001 | Calenzo, Sr. et al. | 607/142 |

* cited by examiner

*Primary Examiner*—George R. Evanisko
(74) *Attorney, Agent, or Firm*—Tony Piotrowski

(57) ABSTRACT

A defibrillation system for patients of all ages may include an Automated External Defibrillator (AED) coupled to a set of universal electrodes. Universal electrodes may be reduced-size versions of adult electrodes, and may include an opening to lower effective impedance. The AED may include an adult/pediatric mode control or switch. Based upon the setting of the adult/pediatric switch, the AED may perform an adult defibrillation sequence or a pediatric defibrillation sequence. An adult defibrillation sequence may comprise delivery of one or more waveforms or shocks characterized by energies appropriate for adults, for example, 150 Joule biphasic waveforms. A pediatric defibrillation sequence may comprise delivery of one or more waveforms characterized by energies appropriate for children, for example, 50 Joule biphasic waveforms. Another pediatric defibrillation sequence may comprise delivery of an escalating low-energy shock sequence to a patient, such as a 25 to 50 Joule shock, followed by a 65 to 75 Joule shock as necessary, followed by one or more 100 Joule shocks as necessary.

19 Claims, 4 Drawing Sheets

METHOD AND APPARATUS FOR DEFIBRILLATING PATIENTS OF ALL AGES

BACKGROUND OF THE INVENTION

1. Field of the Invention

The present invention relates generally to an electrotherapy apparatus and method for delivering a series of shocks to a patient's heart. More particularly, this invention is an Automated External Defibrillator (AED) suitable for defibrillating patients of all ages.

2. Description of the Prior Art

Sudden Cardiac Arrest (SCA) is one of the leading causes of death in the industrialized world, and typically results from an arrhythmia condition known as Ventricular Fibrillation (VF), during which a patient's heart muscle exhibits extremely rapid, uncoordinated contractions that render the heart incapable of circulating blood. Statistically, after the first four minutes, the patient's chance of survival decreases by 10% during each subsequent minute they fail to receive treatment.

An effective treatment for VF is electrical defibrillation, in which a defibrillator delivers an electrical pulse or shock to the patient's heart. Because the onset of VF is generally an unpredictable event, the likelihood that a victim will survive rises dramatically if defibrillation equipment is nearby. As a result, medical equipment manufacturers have developed Automated External Defibrillators (AEDs) that minimally trained personnel may employ to perform electrical defibrillation when emergency situations arise. AEDs may be found in non-medical settings such as residences, public buildings, businesses, private vehicles, public transportation vehicles, and airplanes.

To increase a patient's chances of survival, AED operators must perform quickly and accurately in life-threatening situations. Hence, AEDs are typically designed to be simple and intuitive to use. AEDs often automate many of the steps associated with operating external defibrillation equipment, and minimize the number of decisions the operator must make. An AED may provide voice instructions or commands to guide the operator through application of the device. Typically, an AED automatically analyzes a patient's heart rhythm, and determines when administration of an electrical shock to the patient is appropriate. If a shock is warranted, the AED facilitates delivery of a defibrillation waveform at a particular energy level.

The vast majority of VF situations involve adult patients, as VF tends to be a rare condition in children. Nonetheless, recent evidence suggests that pediatric VF occurs with sufficient frequency to be of concern. AEDs, however, are designed for use on adults. In the past, pediatric application of AEDs had been limited by a lack of data characterizing pediatric Electrocardiogram (ECG) rhythms, which cast doubt upon the effectiveness of EGG detection algorithms that an AED may employ in pediatric situations.

Energy delivery recommendations for children are dependent upon body mass, whereas such recommendations for adults are not. Presently, the recognized treatment for pediatric VF in children less than 8 years of age is manual defibrillation in which delivered energies are proportional to the patient's body weight (1 Joule per kilogram of body weight, increasing to 2 Joules per kilogram if necessary). Incorporating controls to facilitate detailed energy adjustments in accordance with body mass or weight would add extra complexity and cost to AED design. More importantly, providing such controls would undesirably complicate the decisions operators must make during time-critical situations, even when treating adults, thereby providing more opportunity for treatment to fail.

Present defibrillators require differently-sized electrodes for children and adults. Pediatric electrodes are typically 15 to 45 square centimeters each in area, whereas adult electrodes typically exhibit considerably larger areas, for example, 75 to 100 square centimeters each. Unfortunately, adult electrodes are too large to easily place or position upon small children or infants. Conversely, the use of pediatric electrodes upon adult patients may present a total impedance that is too large for effective use. Thus, with the present art, emergency responders must undesirably choose an electrode size appropriate for the victim being treated.

AEDs are typically deployed with electrodes sized for adults rather than children. However, some AEDs include electrodes specifically designed for pediatric use. An AED such as that described in U.S. Pat. No. 6,134,468, entitled "Method and Apparatus for Reducing Defibrillation Energy," which is incorporated herein by reference, includes pediatric size electrodes that are coupled to a connector that attenuates adult shock energies. Such a pediatric electrode and connector configuration facilitates the delivery of a reduced-energy shock to a pediatric patient. While an AED could be stocked with one set of electrodes suitable for adults plus another set of electrodes suitable for children, this would undesirably present operators with another series of choices to make during life-threatening VF situations.

What is needed is a defibrillation system capable of treating all human beings with equal ease, regardless of age.

SUMMARY OF THE INVENTION

An Automated External Defibrillator (AED) may include an adult/pediatric mode control or switch. Based upon a setting of the adult/pediatric switch, the AED may perform an adult defibrillation sequence or a pediatric defibrillation sequence upon a patient. An adult defibrillation sequence may involve the delivery of one or more defibrillator shocks characterized by an energy appropriate for adults. For example, an adult defibrillation sequence may comprise the delivery of one or more 150 Joule biphasic waveforms to the patient.

A pediatric defibrillation sequence may involve the delivery of one or more defibrillator shocks characterized by an energy appropriate for children who are or seem to be less than eight years of age. For example, a pediatric defibrillation sequence may comprise the delivery of one or more 50 Joule biphasic defibrillator shocks to the patient.

A pediatric defibrillation sequence may alternatively or additionally involve the delivery of one or more escalating-energy waveforms to the patient. Such a pediatric defibrillation sequence may comprise, for example, delivery of a 25 to 50 Joule biphasic waveform to the patient; followed by delivery of a 65 to 75 Joule biphasic waveform, if necessary; followed by delivery of one or more 100 to 115 Joule biphasic waveforms, if necessary.

A universal electrode may comprise an electrode that is smaller than a conventional adult electrode, yet larger than a conventional pediatric electrode. The universal electrode may include an opening for the purpose of reducing its effective impedance.

DESCRIPTION OF THE PREFERRED EMBODIMENTS

The following discussion is presented to enable a person skilled in the art to make and use the invention. The general principles described herein may be applied to embodiments and applications other than those detailed below without departing from the spirit and scope of the present invention as defined by the appended claims. The present invention is not intended to be limited to the embodiments shown, but is to be accorded the widest scope consistent with the principles and features disclosed herein.

AED Architecture

Figure 1:
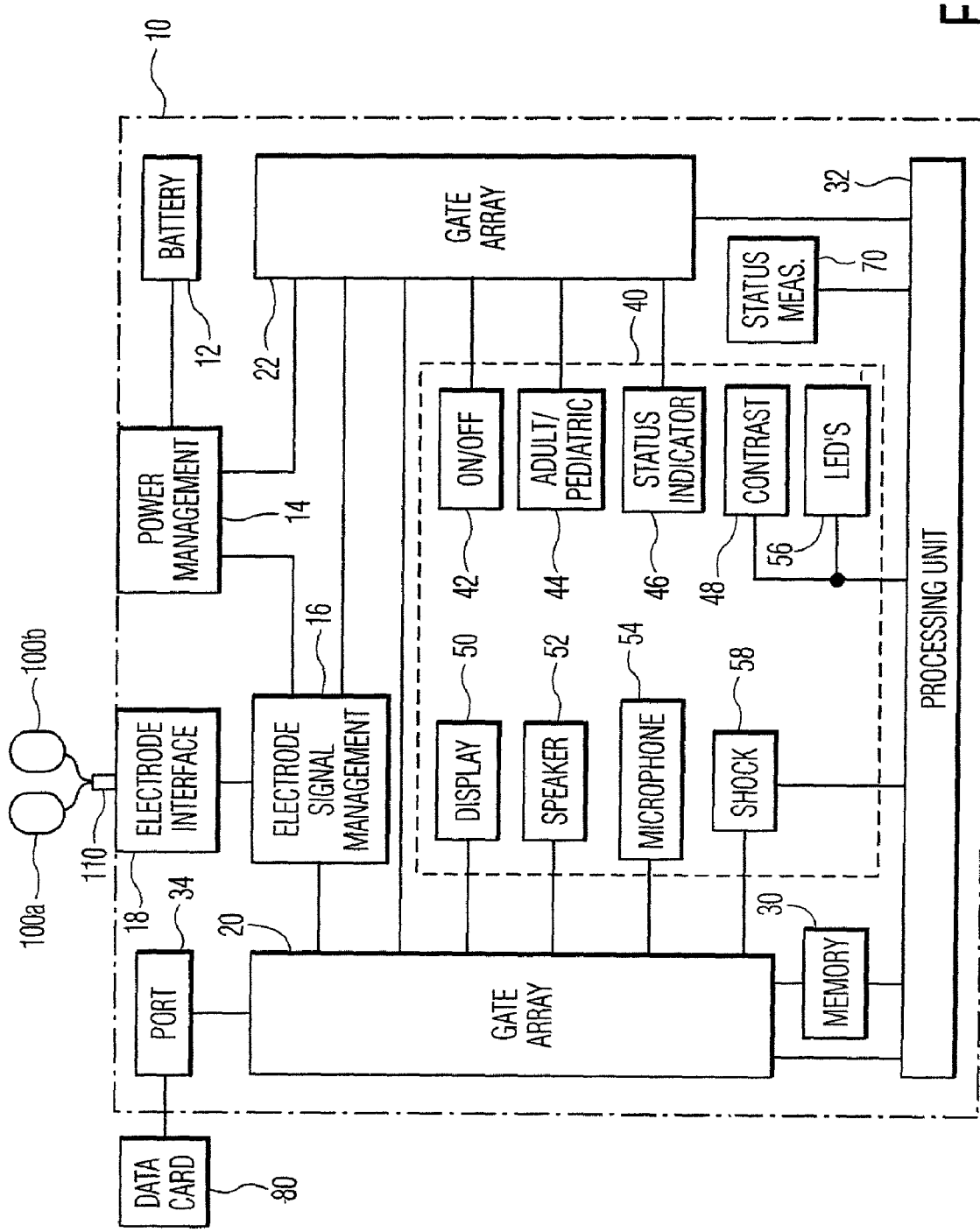
FIG. 1 is a schematic block diagram of an Automated External Defibrillator constructed in accordance with the present invention.

FIG. 1 is a block diagram of a universal AED 10 according to an embodiment of the present invention. The AED 10 comprises a power source or battery 12; a power management unit 14; an electrode signal management unit 16; an electrode interface 18; a first and a second gate array 20, 22; a memory 30; a processing unit 32; a communication interface or port 34; an operator interface 40 that includes a power or on/off switch 42, an adult/pediatric mode control or switch 44, a status indicator 46, a contrast control 48, a display 50, a speaker 52, a microphone 54, a set of Light Emitting Diodes (LEDs) 56, and a shock button 58; and a status measurement unit 70.

The on/off switch 42 may turn the AED 10 on or off in a conventional manner. The status indicator 46 indicates the AED's operational status. The adult/pediatric switch 44 may comprise a switch that specifies an AED operational mode depending upon switch setting. The adult/pediatric switch 44 may facilitate operator specification of whether a patient is an adult or a child less than eight years of age. Depending upon a setting indicated by the adult/pediatric switch 44, the AED 10 may perform an adult or a pediatric defibrillation sequence, as detailed below. The AED 10 may power-up or initialize in an adult treatment mode, and change to a pediatric treatment mode in response to an AED operator adjusting or setting the adult/pediatric switch 44. In one embodiment, the adult/pediatric switch 44 comprises a keyed switch, which requires a key turn to place the AED 10 into the pediatric treatment mode.

The electrode interface 18 may be coupled to a plurality of electrodes 100a, 100b via a connector 110. The electrodes 100a, 100b are operable to sense a patient's ECG (not shown) and deliver an electrical waveform or shock to the patient (not shown). Electrode embodiments having universal applicability to both adults and children are described below with reference to FIGS. 2A and 2B.

The electrode signal management unit 16 exchanges signals with the electrodes 100a, 100b via the electrode interface 18. During an analysis mode of operation, the electrode signal management unit 16 samples the patient's ECG. During a shock delivery mode of operation, the electrode signal management unit 16 provides a shock to the patient. The electrode signal management unit 16 may provide different types of shock sequences to the patient depending upon a setting indicated by the adult/pediatric switch 44, as described in detail below. The electrode signal management unit 16 may include impedance compensation circuitry, such as that described in U.S. Pat. No. 6,047,212, entitled "External Defibrillator Capable of Delivering Patient Impedance Compensated Biphasic Waveforms," which is incorporated herein by reference.

The first gate array 20 receives ECG samples from the electrode signal management unit 16, and may transfer this information to the memory 30 and/or the processing unit 32. The memory 30 may comprise one or more types of Random Access Memory (RAM) and Read-Only Memory (ROM), including Programmable ROM (PROM). The memory 30 stores data, plus program instruction sequences that direct the operation of the processing unit 32 and the gate arrays 20, 22. Such program instruction sequences may direct the defibrillation of adult and pediatric patients in the manners described in detail below.

The processing unit 32 may analyze ECG samples, and determine whether the patient is suffering from a shockable heart rhythm. If the patient is suffering from a shockable heart rhythm, the processing unit 32 instructs the electrode signal management unit 16 to enable delivery of an appropriate shock when an operator (not shown) presses the shock button 58. If the processing unit 32 determines that the patient is not suffering from a shockable heart rhythm, the processing unit 32 may disable the electrode signal management unit's shock delivery capabilities to prevent delivery of a shock to the patient.

The power management unit 14 distributes power from the battery 12 to each of the AED's subsystems and/or subcircuits. The second gate array 22 interfaces the power management unit 14, the on/off switch 42, the adult/pediatric switch 44, and the status indicator 46 to the electrode signal management unit 16, the first gate array 20, and the processing unit 32.

The display 50 presents visual information to the operator, who may adjust display characteristics via the contrast control 48. The LEDs 56 may also provide information to the operator, such as whether the processing unit 32 has enabled the electrode signal management unit 16 to deliver a shock to the patient. The speaker 52 may provide audio instructions to the operator, and the microphone 54 may record the operator's voice and/or other audible sounds. The display 50 and/or the speaker 52 may present instructions to the operator relative to setting the adult/pediatric switch 44. Such instructions may indicate, for example, that the adult/pediatric switch 44 should be set, moved, or turned to a pediatric mode position in the event that the patient is a child that is or seems, either to the AED operator or the AED 10 itself, to be less than eight years of age.

The communication port 34 may serve as an interface between the first gate array 20 and a data card 80 or other types of circuitry. In one embodiment, the data card 80 stores the operator's voice and other sounds along with the patient's ECG and a record of AED events for later study. The status measurement unit 70 may monitor the state of various AED subsystems and/or subcircuits, and provides associated status information to the processing unit 32.

Universal Electrodes

One embodiment of the AED system includes the AED 10 of FIG. 1, coupled to a set of universal electrodes having equal applicability to adults and children. Those skilled in the art will recognize that the AED system may include conventional AED electrodes; however, such electrodes are designed for adults and are typically larger than desired for pediatric applications.

Figure 2A:
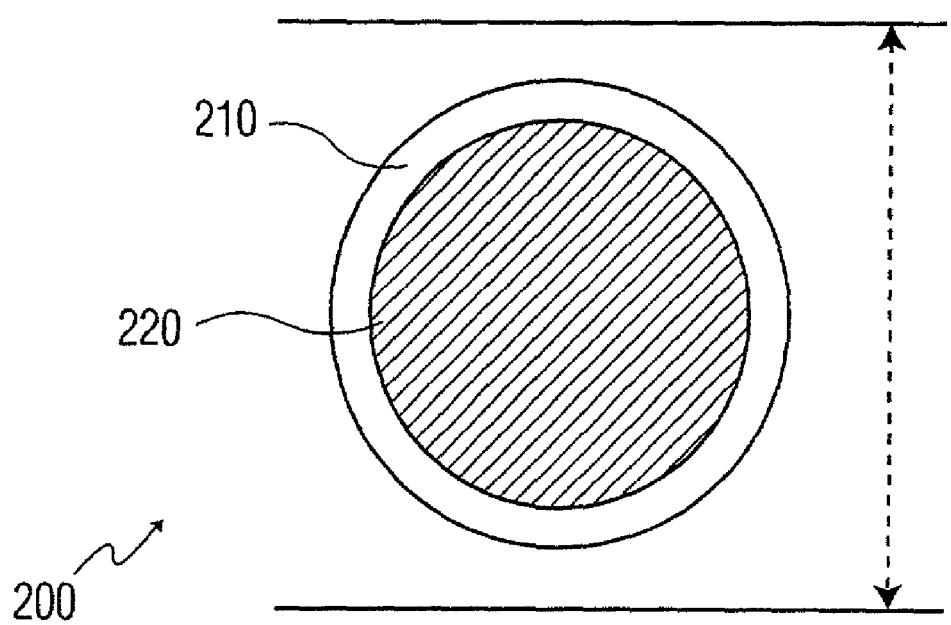
FIG. 2A is a top view of a universal electrode according to an embodiment of the invention.

FIG. 2A is a top view of a universal electrode 200 according to an embodiment of the invention. The universal electrode 200 comprises a reduced-size version of a conventional adult electrode, and is larger than a conventional pediatric electrode. The universal electrode 200 includes a conductive adhesive or hydrogel layer 210 upon which a foil layer 220 resides, in a manner readily understood by those skilled in the art. A dashed line 230 in FIG. 2A provides an indication of the size of the universal electrode 200 relative to a standard adult electrode. In one embodiment, the universal electrode 200 has a surface area equal or approximately equal to 50 square centimeters. Those skilled in the art will recognize that various implementations of the universal electrode 200 may exhibit a range of surface areas or sizes.

As electrode area and/or perimeter decreases, the effective impedance between the electrode and the patient increases. Those skilled in the art will understand that impedance compensation circuitry such as that referenced above with respect to FIG. 1 may ensure efficient delivery of a predetermined amount of energy in an effective waveform across the universal electrode 200 for both adult and pediatric patients. Alternatively or additionally, variations in electrode design may significantly reduce effective impedance, as described in detail hereafter.

Figure 2B:
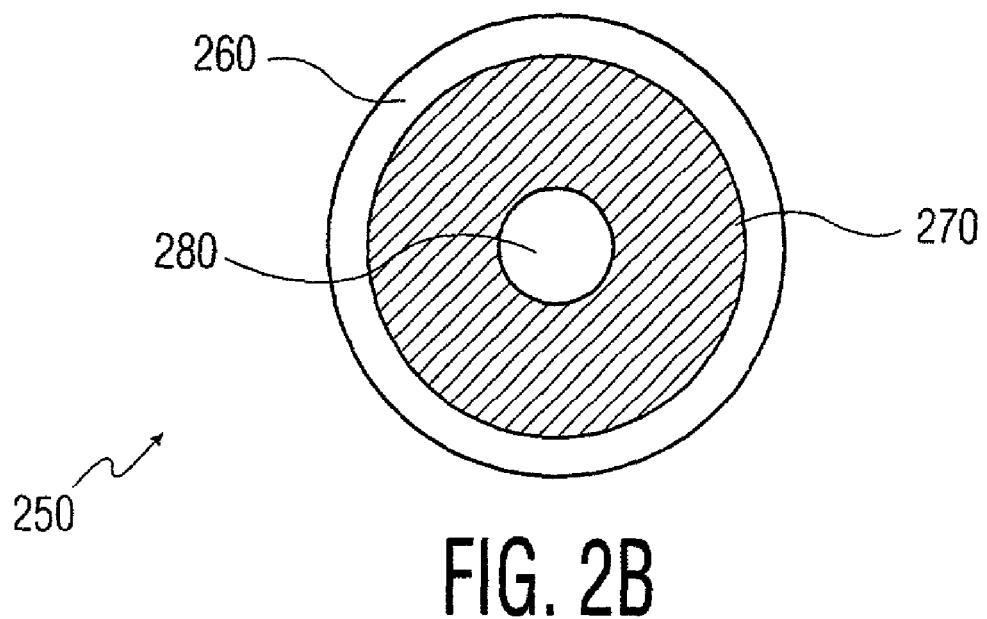
FIG. 2B is a top view showing a universal electrode according to another embodiment of the invention.

FIG. 2B is a top view showing a universal electrode 250 according to another embodiment of the invention. In one embodiment, the universal electrode 250 comprises a conductive adhesive or hydrogel layer 260 and a foil layer 270 having an opening 280 disposed therein. Such an electrode is described in detail in U.S. Pat. No. 6,694,193, entitled "Medical Electrode and Release Liner Configurations Facilitating Packaged Electrode Characterization," filed on Sep. 14, 2001, which is commonly owned and incorporated herein by reference. In a manner analogous to the universal electrode 200 of FIG. 2A, the universal electrode 250 of FIG. 2B may be smaller than a standard adult electrode.

In one embodiment, the opening 280 is generally circular, and has a diameter of approximately 25 to 40 millimeters. Those skilled in the art will recognize that in various embodiments, the universal electrode 250 may have differently sized, differently shaped, and/or multiple openings. Relative to the universal electrode 200 of FIG. 2A, the presence of the opening 280 reduces effective impedance by altering the nature of current flow between the universal electrode 250 and a patient's body (not shown).

Figure 2C:
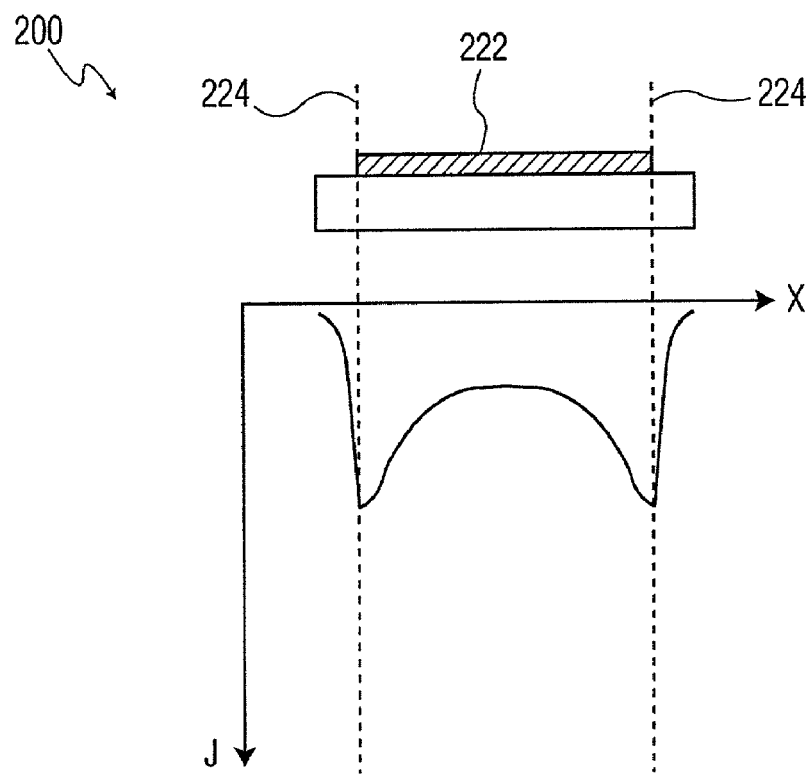
FIG. 2C is a graph showing exemplary skin surface current density relative to lateral position beneath the universal electrode of FIG. 2A.

FIG. 2C is a graph showing exemplary skin surface current density (J) relative to lateral position (x) beneath the universal electrode 200 of FIG. 2A, where the universal electrode 200 is shown in a cross-sectional view. It has been found that the current flows more easily between an electrode and a patient's body near the electrode's edges. As one moves from an interior region 222 toward an outer edge or border 224 of the universal electrode's foil layer 220, current density increases and peaks.

Figure 2D:
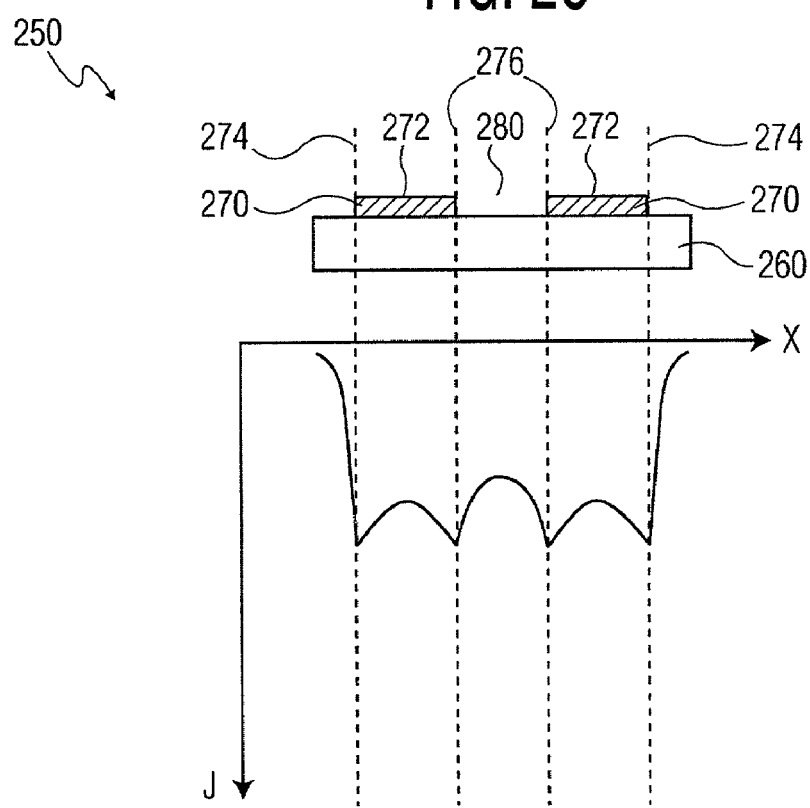
FIG. 2D is a graph showing exemplary skin surface current density relative to lateral position beneath the universal electrode of FIG. 2B.

FIG. 2D is a graph showing exemplary skin surface current density (J) relative to lateral position (x) beneath the universal electrode 250 of FIG. 2B, where the universal electrode 250 is shown in a cross-sectional view. The universal electrode's foil layer 270 includes an outer edge 274 and an inner edge 276. As one moves from an interior region 272 toward either of the foil layer's outer or inner edges 274 or 276, current density increases and peaks.

The current density beneath the universal electrode 200 of FIG. 2A exhibits peaks only in the vicinity of its foil layer's outer edge 224. However, the current density beneath the universal electrode 250 of FIG. 2B exhibits peaks proximate both its foil layer's outer and inner edges 274 and 276. This, in turn, advantageously reduces the effective impedance of the universal electrode 250. Those skilled in the art will recognize that the area under the curve shown in FIG. 2D may be greater than the area under the curve shown in FIG. 2C, indicating a reduced net impedance for the universal electrode 250 of FIG. 2B relative to that for the universal electrode 200 of FIG. 2A.

Defibrillation Methods

Figure 3:
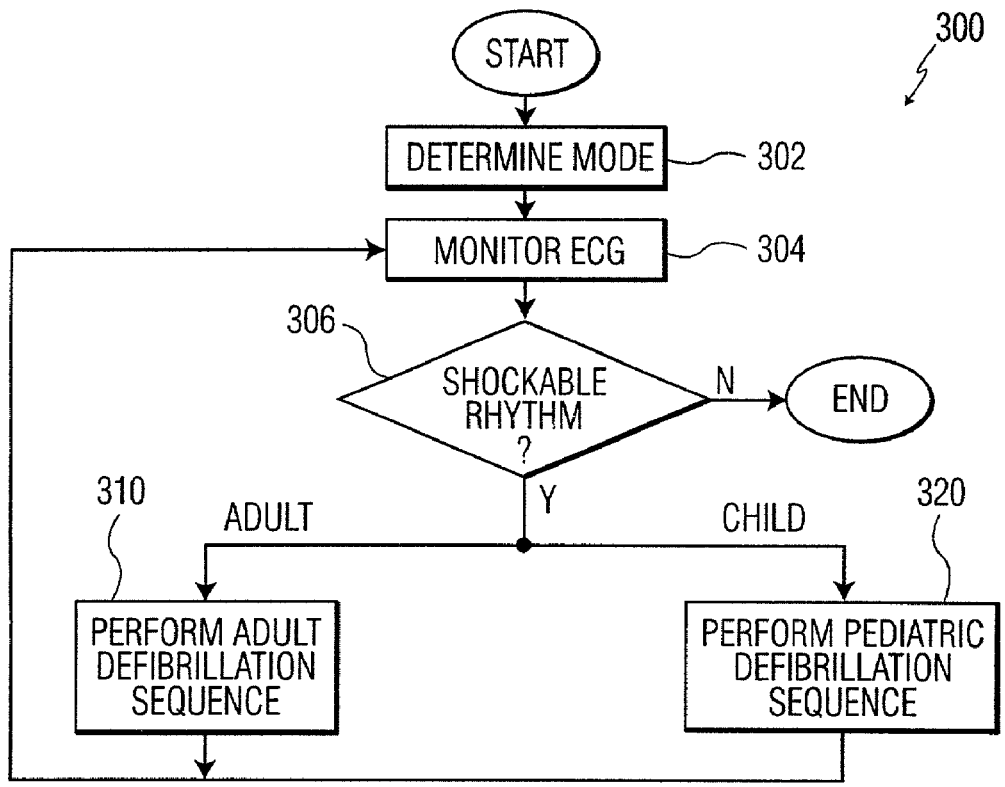
FIG. 3 is a flowchart of a procedure for defibrillating patients of all ages according to an embodiment of the invention.

FIG. 3 is a flowchart of a procedure 300 for defibrillating patients of all ages in accordance with an embodiment of the invention. In one embodiment, the procedure 300 begins in step 302 by determining whether the adult/pediatric switch 44 is set to indicate an adult mode or a pediatric mode. Next, the procedure 300 monitors a patient's ECG in step 304. In one embodiment, the procedure 300 may employ different ECG monitoring techniques based upon the setting of the adult/pediatric switch 44.

The procedure 300 next determines whether the patient is suffering from a shockable heart rhythm in step 306. If not, the procedure 300 may end. If the patient is suffering from a shockable heart rhythm, the procedure 300 initiates or performs a defibrillation sequence based upon the setting of the adult/pediatric switch 44. If the patient is an adult, the procedure 300 may enable delivery of a first or next shock in an adult defibrillation sequence in step 310. The adult defibrillation sequence may comprise delivery of one or more shocks to the patient, where such shock waveforms may be characterized by energy levels appropriate for adults. For example, the adult defibrillation sequence may deliver one or more biphasic waveform shocks having an energy of 150 Joules to the patient. An adult defibrillation sequence may alternatively or additionally comprise delivery of one or more escalating energy shocks or waveforms to the patient, where such shocks may be characterized by energies appropriate for adults.

If the patient is a child, where the child is or seems to be less than eight years of age, the procedure may enable delivery of a first or next shock in a pediatric defibrillation sequence in step 320. The pediatric defibrillation sequence may comprise delivery of one or more low-energy waveforms to the patient, such as 50 Joule biphasic waveforms. During one or more of the above steps, the procedure 300 may perform impedance measurement and compensation operations in a conventional manner. Following either of steps 310 or 320, the procedure 300 returns to step 304.

Figure 4:
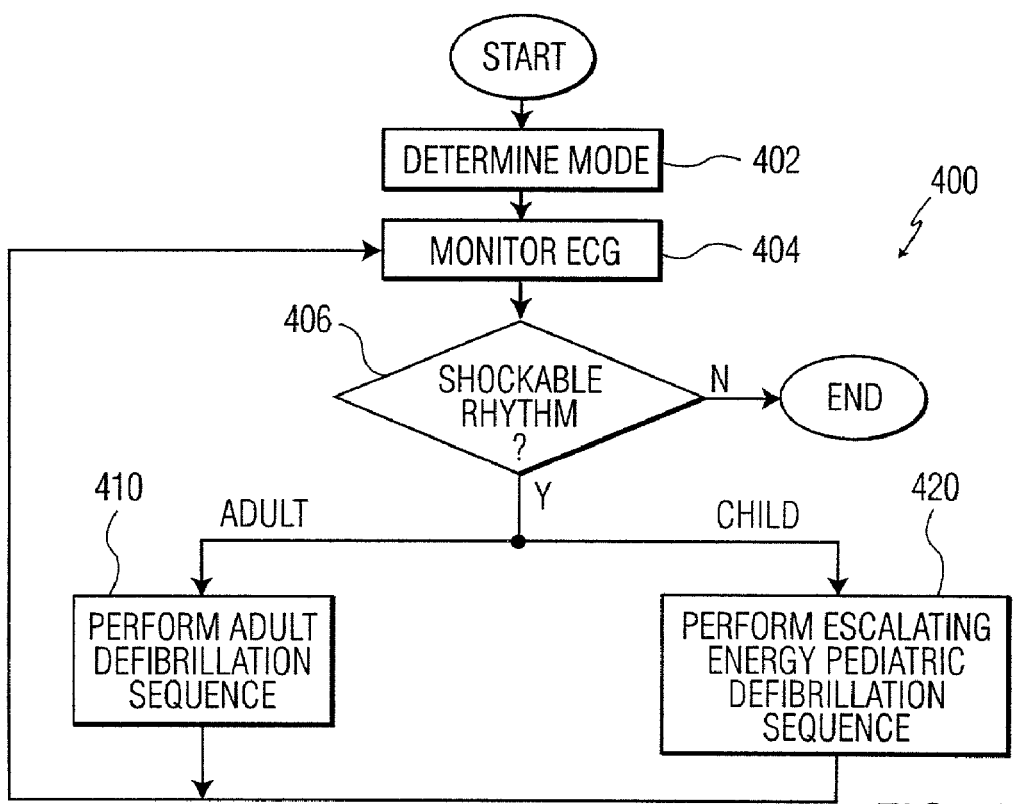
FIG. 4 is a flowchart of a procedure for defibrillating patients of all ages according to another embodiment of the invention.

FIG. 4 is a flowchart of a procedure 400 for defibrillating patients of all ages in accordance with another embodiment of the invention. The procedure 400 begins in step 402 by determining whether the adult/pediatric switch 44 is set to indicate an adult mode or a pediatric mode. Next, the procedure 400 monitors a patient's ECG in step 404. In one embodiment, the procedure 400 may employ different ECG monitoring techniques based upon the setting of the adult/pediatric switch 44.

The procedure 400 next determines whether the patient is suffering from a shockable heart rhythm in step 406. If not, the procedure 400 may end. If the patient is suffering from a shockable heart rhythm, the procedure 400 initiates or performs a defibrillation sequence based upon the setting of the adult/pediatric switch 44. If the patient is an adult, the procedure 400 may enable delivery of a first or next shock in an adult defibrillation sequence in step 410. The adult defibrillation sequence may comprise delivery of one or more shock waveforms to the patient, where such shock waveforms may be characterized by energy levels appropriate for adults. For example, the adult defibrillation sequence may deliver one or more biphasic shock waveforms having an energy of 150 Joules to the patient. An adult defibrillation sequence may alternatively or additionally comprise delivery of a series of escalating energy shocks or waveforms to the patient, where such shocks may be characterized by energies appropriate for adults.

If the patient is a child, where the child is or seems to be less than eight years of age, the procedure may enable delivery of a first or next shock in an escalating energy pediatric defibrillation sequence in step 420. An escalating energy pediatric defibrillation sequence may begin with a shock having a low or generally low energy, possibly followed by one or more shocks of higher energy until defibrillation is successful and/or a maximum target shock energy is reached. The escalating energy pediatric defibrillation sequence may comprise delivery of, for example, a 25 to 50 Joule biphasic waveform, followed by a 65 to 75 Joule biphasic waveform (if necessary), followed by one or more 100 to 115 Joule biphasic waveforms (if necessary). Those skilled in the art will recognize that other escalating low-energy shock sequences characterized by different energies and/or a different number of energy increments may be employed in alternate embodiments. Such low-energy shock sequences may be defined in accordance with an energy increment plan. Additionally, if a patient relapses in to a shockable heart rhythm condition following a successful defibrillation, the procedure 400 may begin subsequent shock delivery using a most-recently successful shock energy. During one or more of the above steps, the procedure 400 may perform impedance measurement and compensation operations in a conventional manner. Following either of steps 410 or 420, the procedure 400 returns to step 404.

What is claimed is:

1. A method comprising the steps of:
   coupling a patient to an AED via a pair of identical universal electrodes suitable for use upon both adults and children which have a total area smaller than conventional adult electrodes and larger than conventional pediatric electrodes for delivering the energy level produced by the AED to a patient;
   identifying to the AED whether the patient is an adult or a child by operator setting of an operator adjustable adult/pediatric mode indicator;
   electronically determining whether the patient requires defibrillation;
   producing in the AED an energy level appropriate for an adult in the event that the patient is identified as an adult;
   delivering a first electrical waveform via the universal electrodes which is characterized by the energy level appropriate for an adult in the event that the patient is an adult;
   producing in the AED an energy level appropriate for a child in the event that the patient is identified as a child; and
   delivering a second electrical waveform via the universal electrodes which is characterized by the energy level appropriate for a child in the event that the patient is a child.

2. The method of claim 1,
   wherein identifying comprises determining that the patient is a child; and
   wherein delivering comprises delivering a second electrical waveform characterized by less than or equal to approximately 150 Joules of energy to the patient.

3. The method of claim 2,
   wherein the universal electrode comprises an electrode having a foil layer with an opening disposed therein.

4. The method of claim 2 further comprising the step of:
   compensating for patient-dependent impedance during electrical waveform delivery,
   wherein the universal electrode comprises an electrode having a foil layer with an opening disposed therein.

5. The method of claim 1,
   wherein identifying comprises determining that the patient is a child; and
   wherein delivering comprises delivering the second electrical waveform characterized by greater than approximately 25 Joules and less than approximately 50 Joules of energy to the patient.

6. The method of claim 5 further comprising the step of determining whether defibrillation was successful.

7. The method of claim 5 further comprising the steps of:
   determining whether defibrillation was successful; and
   delivering a further electrical waveform characterized by an energy greater than that associated with the previous electrical waveform to the patient.

8. The method of claim 5 further comprising the steps of:
   determining whether defibrillation was successful; and
   delivering a further electrical waveform characterized by an energy greater than that associated with the previous electrical waveform to the patient,
   wherein the further electrical waveform is characterized by an energy greater than 50 Joules.

9. The method of claim 5,
   wherein the universal electrode comprises an electrode having a foil layer with an opening disposed therein.

10. The method of claim 1,
    wherein identifying comprises determining that the patient is a child;
    wherein delivering comprises delivering the second electrical waveform characterized by an energy greater than approximately 25 Joules and less than approximately 50 Joules to the patient;
    further comprising determining whether defibrillation was successful; and
    further comprising successively delivering higher-energy electrical waveforms to the patient until a delivery of an electrical waveform characterized by a maximum energy target occurs.

11. The method of claim 10, wherein the step of successively delivering higher-energy electrical waveforms to the patent is performed according to an energy increment plan.

12. The method of claim 10, wherein the maximum energy target equals approximately 100 Joules.

13. The method of claim 10, wherein the universal electrode comprises an electrode having a foil layer with an opening disposed therein.

14. The method of claim 10, wherein setting an adult/pediatric mode indicator further comprises determining whether a first electrical waveform or a second electrical waveform is to be produced by a defibrillator.

15. The method of claim 14, wherein setting an adult/ pediatric mode indicator further comprises setting an adult/ pediatric mode switch.

16. The method of claim 1, wherein the first electrical waveform is characterized by an energy of approximately 150 Joules.

17. The method of claim 1, wherein the second electrical waveform is characterized by an energy of approximately 50 Joules.

18. The method of claim 1, wherein setting an adult/ pediatric mode indicator further comprises determining whether a first electrical waveform or a second electrical waveform is to be produced by a defibrillator.

19. The method of claim 1, wherein setting an adult/ pediatric mode indicator further comprises setting an adult/ pediatric mode switch.

* * * * *